(12) United States Patent
Köhler

(10) Patent No.: US 6,438,198 B1
(45) Date of Patent: Aug. 20, 2002

(54) COMPUTED TOMOGRAPHY METHOD

(75) Inventor: Thomas Köhler, Norderstedt (DE)

(73) Assignee: Koninklijke Philips Electronics N. V., Eindhoven (NL)

( * ) Notice: Subject to any disclaimer, the term of this patent is extended or adjusted under 35 U.S.C. 154(b) by 0 days.

(21) Appl. No.: 09/718,249

(22) Filed: Nov. 22, 2000

(30) Foreign Application Priority Data

Nov. 25, 1999 (DE) .......................................... 199 56 585

(51) Int. Cl.$^7$ ................................................. A61B 6/03
(52) U.S. Cl. ........................................... 378/15; 378/19
(58) Field of Search ............................. 378/15, 19, 4, 378/14

(56) References Cited

U.S. PATENT DOCUMENTS

| | | | |
|---|---|---|---|
| 4,504,962 A | * | 3/1985 | Moore .......................... 378/19 |
| 6,118,839 A | * | 9/2000 | Dafni et al. ................... 378/15 |
| 6,259,766 B1 | * | 7/2001 | Cuppen ....................... 378/147 |
| 6,269,141 B1 | * | 7/2001 | Proksa et al. ................. 378/19 |

FOREIGN PATENT DOCUMENTS

GB 2005995 4/1979 .......... G01N/23/06

\* cited by examiner

Primary Examiner—Robert H. Kim
Assistant Examiner—Irakli Kiknadze
(74) Attorney, Agent, or Firm—John Vodopia

(57) ABSTRACT

A computed tomography method in which novel compromise is reached between transmission bandwidth and image quality. The method includes combining the signals of at least two neighboring detector elements so as to form one measured value, and cyclically varying the combinations of neighboring detector element signals as the radiation source position changes.

9 Claims, 4 Drawing Sheets

COMPUTED TOMOGRAPHY METHOD

BACKGROUND OF THE INVENTION

Figure 1:
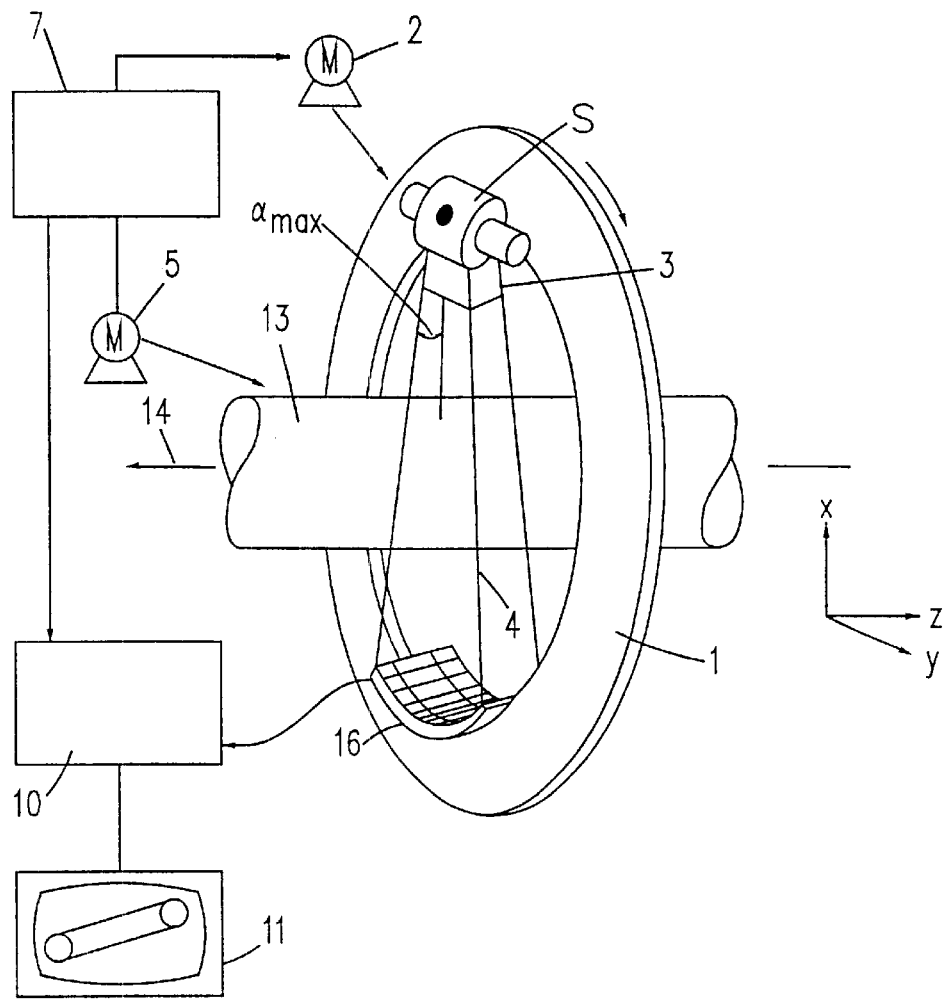

The invention relates to a computed tomography method which includes the steps of: generating, using a radiation source, a radiation beam which traverses an examination zone or an object present therein, generating a relative motion, including a rotation about an axis of rotation, between the radiation source on the one side and the examination zone or the object on the other side, acquiring measured values for a plurality of radiation source positions by means of a detector unit which is coupled to the radiation source and includes at least one row of detector elements.

The invention also relates to a computed tomography apparatus for carrying out the method.

The number of read-out channels in a computed tomography apparatus is limited because of the costs of the data acquisition, the transmission bandwidth of the data slip ring and/or the data throughput that can be handled by a reconstruction unit. For example, in the case of a computed tomography apparatus which rotates around an examination zone three times per second with a detector unit which acquires data from 1400 different angular positions during each rotation and comprises 16 rows of 1000 detector elements each, the measured values must be transferred and evaluated with a transmission bandwidth of approximately 200 Mbyte/second (assuming that a measured value of 3 bytes is transferred). This would only be possible, if possible at all, at high costs.

GB 2,005,955 already discloses a computed tomography apparatus of the kind set forth in which the signals from two or more detector elements at the edge of the detector unit are combined. Thus, fewer measured values need be transferred to the reconstruction unit reconstructing computed tomograms from the measured values; however, this reduction is achieved at the expense of the spatial resolution at the edges of the examination zone at least.

Such a combination of signals would lead to a further reduction of the resolution in computed tomography apparatus including the meanwhile customary so-called "quarter detector shift" (where the detector unit is arranged relative to the radiation source and the axis of rotation in such a manner that the projections of the axis of rotation on the detector unit are shifted one quarter of the width of a detector element relative to the center of the detector unit), because the advantages associated with the quarter detector shift can no longer be utilized.

OBJECTS AND SUMMARY OF THE INVENTION

It is an object of the present invention to propose a computed tomography method of the kind set forth such that a more attractive compromise is reached between the number of measured values to be measured/transmitted and/or processed on the one hand and the image quality on the other hand.

On the basis of a computed tomography method of the kind set forth this object is achieved according to the invention in that the method also includes the following steps:

combining the signals of each time at least two neighboring detector elements so as to form one measured value, and cyclically varying the combinations from one radiation source position to another.

The invention is based on the following considerations.

Each detector element in a detector unit has several neighboring detector elements. Thus, the output signals of the detector elements can be combined in various manners. As has already been explained, each combination per se would lead to a reduction of the resolution. However, if dynamic switching over takes place from one of said combinations to another upon changing over from one radiation source position to the next position in such a manner that the combinations are cyclically run through, only a small loss of spatial resolution will occur. This is because the combinations supplement one another in such a manner that the measured values are distributed in the Radon space in substantially the same way as in the absence of these signal combinations.

A computed tomography apparatus for carrying out the method according to the invention includes a radiation source for generating a radiation beam which traverses an examination zone or an object present therein, a drive unit for realizing a relative motion, including a rotation about an axis of rotation, between the radiation source on the one side and the examination zone or the object on the other side, a detector unit which is coupled to the radiation source and includes at least one row of detector elements for the acquisition of measured values for a plurality of radiation source positions, wherein the apparatus includes a combination device for combining the signals of each time at least two neighboring detector elements so as to form one measured value, and means for cyclically varying the combinations from one radiation source position to another. An alternative embodiment also concerns a CT apparatus with a so-called cone beam. Even though the advantages of the invention are also achieved when the detector unit has one row only (fan beam CT), the invention has more effect for cone beam CT than for fan beam CT.

Yet another embodiment describes a first possibility for the combination of detector elements. This combination of the signals from neighboring columns (but the same row) is to be used preferably in conjunction with the so-called quarter detector shift. In a separate embodiment, however, the signals from detector elements of neighboring rows can also be combined. The embodiment may also be used in combined form.

The invention will be described in detail hereinafter with reference to the drawings. Therein:

FIG. 1 shows a computed tomography apparatus which is suitable for carrying out the invention.

Figure 3:
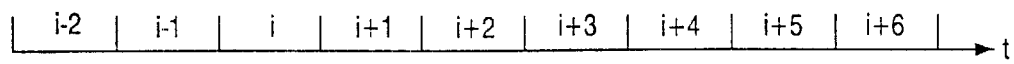
Figure 3:
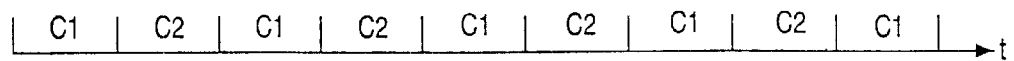
Figure 2A:
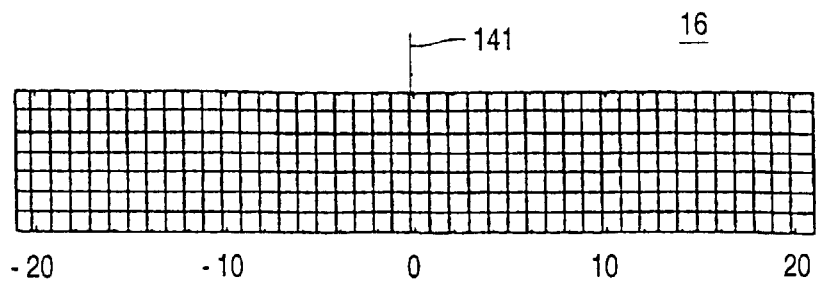
Figure 4A:
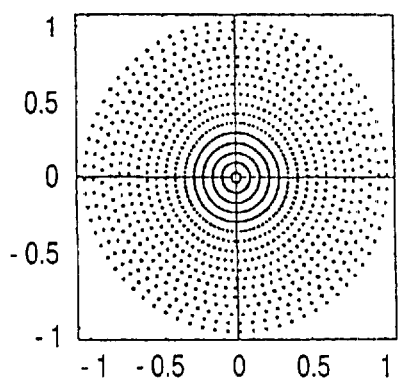
Figure 5A:
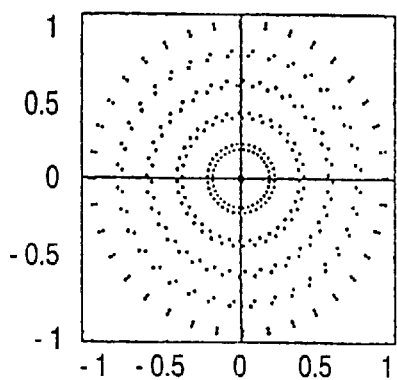
Figure 6A:
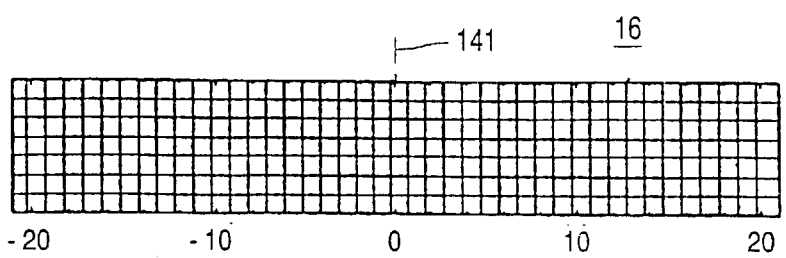
Figure 7:
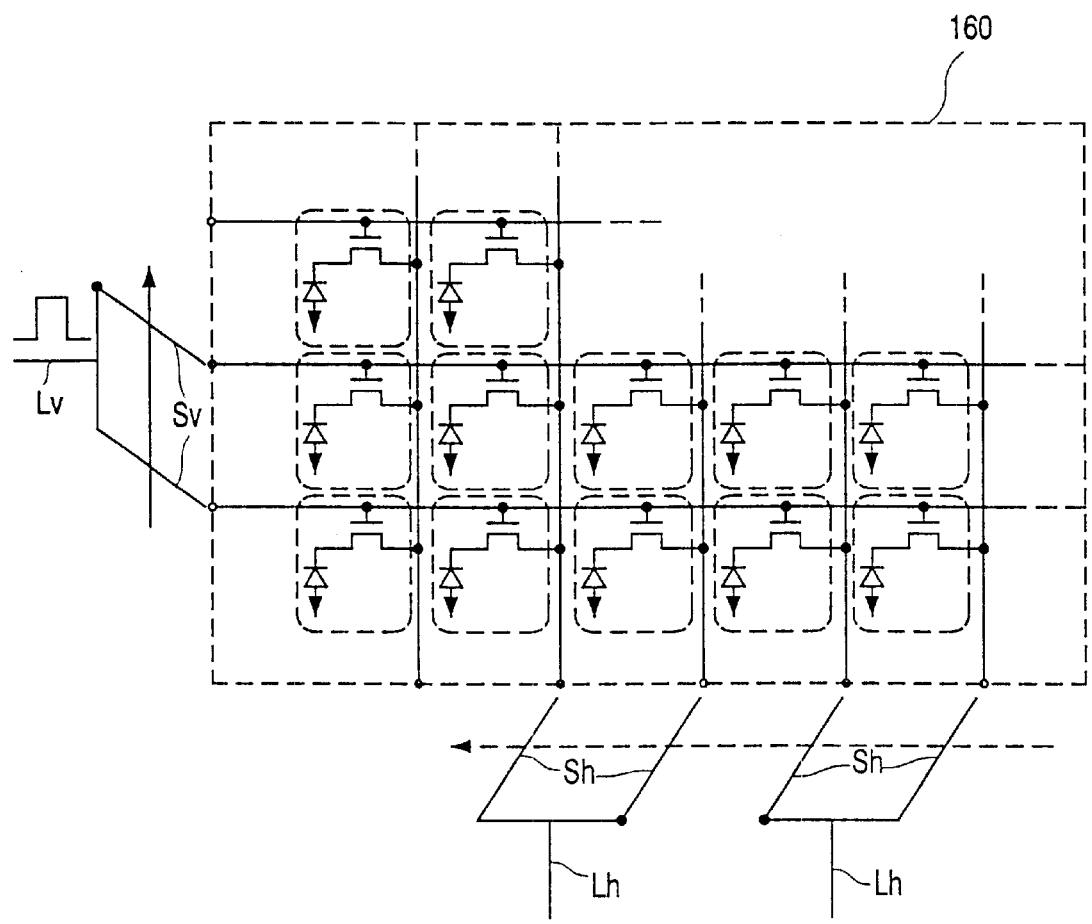

FIGS. 2a) to 2c) show a detector unit and feasible combinations of detector elements, FIG. 3 shows the temporal sequence of the various combinations in successive radiation source positions, FIGS. 4a) to 4d) illustrate the resultant sampling of the Radon space, FIGS. 5a) to 5d) show the sampling of the Radon space in a second embodiment, FIGS. 6a) to 6c) show feasible combinations for a third embodiment, and FIG. 7 diagrammatically illustrates a combination unit for combining the signals from various detector elements.

The computed tomography apparatus shown in FIG. 1 includes a gantry 1 which is capable of rotation about an axis of rotation 14. To this end, the gantry is driven at a preferably constant but adjustable angular speed by a motor 2. A radiation source S, for example an X-ray source, is mounted on the gantry 1. The source is provided with a collimator arrangement 3 which forms a conical radiation beam 4 from the radiation produced by the radiation source 6, that is, a radiation beam having a finite dimension other than zero in a plane perpendicular to the axis of rotation as well as in the direction of the axis of rotation.

The radiation beam 4 irradiates an examination zone 13 in which a patient may be arranged on a patient table (both not shown). The examination zone 13 is shaped as a cylinder. After having traversed the cylinder, the X-ray beam 4 is incident on a two-dimensional detector unit 16 which is mounted on the gantry 1 and includes a plurality of detector elements in a matrix arrangement. Each detector element is capable of supplying a measured value for one ray of the radiation beam 4 in each radiation source position. The detector elements are arranged in rows and columns. The detector rows are situated in planes extending perpendicularly to the axis of rotation, for example on an arc of a circle around the radiation source S. The detector columns extend parallel to the axis of rotation. Generally speaking, the detector rows include a number of detector elements (for example, 1000) which is significantly larger than the number of detector elements in the detector columns (for example, 16).

The angle of aperture $\alpha_{max}$ of the radiation beam 4 (the angle of aperture is to be understood to mean as the angle enclosed by a ray of the beam 4 which is situated at the edge in a plane perpendicular to the axis of rotation 14 relative to a plane defined by the radiation source S and the axis of rotation) then determines the diameter of the cylinder in which the object to be examined must be present during the acquisition of the measured values. The object to be examined, or the patient table (both not shown), can also be displaced parallel to the axis of rotation 14 by means of a motor 5. The speed of this displacement is preferably constant and adjustable. When the motors 5 and 2 are simultaneously activated, the radiation source S and the detector unit 16 perform a helical scanning motion. However, when the motor 5 for the displacement in the direction of the axis of rotation is stationary and the motor 2 rotates the gantry, the X-ray source S and the detector unit perform a circular scanning motion relative to the examination zone. The invention can be used for both scanning motions.

The measured data acquired by the detector unit 16 on the rotating gantry 1 are applied, after combination in conformity with the invention, to an image processing computer 10 which is usually situated in a fixed location in space and is connected to the detector unit via a contactless data slip ring which is not shown.

FIG. 2a) is a simplified representation of a development of the detector unit 16, that is, a representation with a reduced number of rows and columns of detector elements, each of which is represented by a square. Proceeding from the center outwards, the columns are numbered positively and negatively. The reference numeral 141 denotes the line obtained by projection of the axis of rotation 14 through the radiation source S onto the detector unit. This line is at the same time the line of intersection of the detector unit 16 and a plane defined by the radiation source and the axis of rotation. It appears that the center of the detector unit (defined by the outer edge of the two central detector elements in a detector row) has been shifted relative to the line 141 over a distance which corresponds to one quarter of the width of the detector element (quarter detector shift).

FIG. 4a) illustrates the sampling of the Radon space by the central detector row, it being assumed that this detector row includes merely 20 detector elements and that the examination zone consists have been irradiated from 72 regularly distributed radiation source positions (that is, radiation source positions which have been shifted each time 5° relative to the axis of rotation). Each dot represents a measured value of the detector element of the row for one of the radiation source positions. This dot is situated each time at the foot of a perpendicular from the center (0,0) of the Radon space to the ray connecting the radiation source in the relevant radiation source position to said detector element. The center (0,0) is the point of intersection of the plane observed and the axis of rotation. The respective measured value corresponding to the line integral of the absorption along the ray is assigned to this center. The closer the dots are situated in the radial direction in the Radon space, the larger (in the case of uniform scanning of the Radon space) the spatial resolution that can be achieved by reconstruction will be.

According to the embodiment the output signals of each time two detector elements of the same row, but from neighboring columns, are combined. Two combinations are possible. According to the first combination, the output signals of every second detector element of the row are combined with the output signals of the respective right-hand neighboring element. The second possibility for combination consists in combining the output signals of this detector element and its respective left-hand neighboring detector element. The resultant shift of the detector relative to the line 141 amounts to ⅛ and ⅜, respectively; it is to be noted, however, that a ⅜ shift to the left is identical to a ⅝ shift to the right.

Figure 2B:
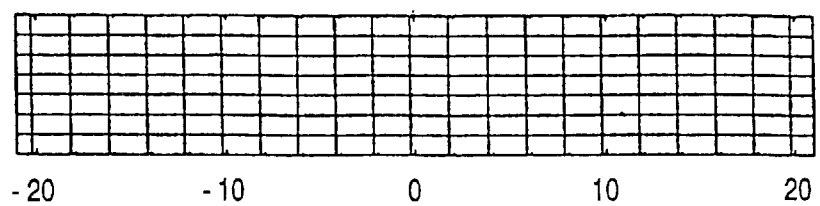

These possibilities for combination are diagrammatically indicated in the FIGS. 2b) and 2c), the detector elements whose output signals are combined being symbolized by a common rectangle in comparison with FIG. 2a). It appears that the rectangles in FIG. 2b) are shifted over the width of one detector element (in FIG. 2a)) relative to the rectangles of FIG. 2c).

FIG. 3c) shows the execution in time of the data acquisition. The first line represents the relevant radiation source position i−2, i−1, i, i+1, ..., i+6 as a function of time. The second line shows which of the two possible combinations has been selected; c1 stands, for example for the combination of FIG. 2b) whereas c2 stands for the combination of FIG. 2c). It appears that from one radiation source position to another cyclical switching over between these two combinations takes place.

Figure 4B:
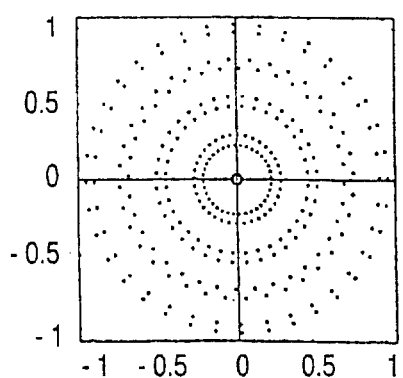

FIG. 4b) shows the scanning of the Radon space by the device shown in FIG. 2b). The number of radiation source positions (36) has been halved, in comparison with FIG. 4a), like the number of measured values per radiation source position (10). It appears that the Radon space is now irregularly sampled in the radial direction, leading to a reduction of the spatial resolution.

Figure 2C:
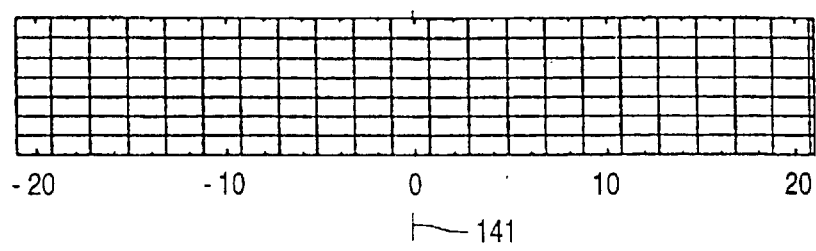
Figure 4C:
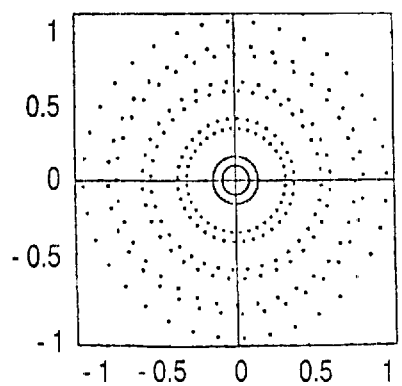

FIG. 4c) shows the corresponding diagram in the Radon space for the 36 intermediate radiation source positions while using the device of FIG. 2c).

Figure 4D:
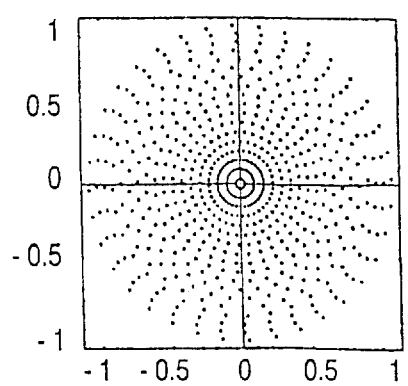

Finally, FIG. 4d) illustrates the sampling of the Radon space which occurs when continuous switching over between the two combinations takes place in conformity with FIG. 3. It appears that in the radial direction the Radon space is sampled practically as good as in FIG. 4a), even though only half the number of measured values is produced due to the combination of measured values.

The combination of output signals of neighboring detector elements has the same effect, as has already been stated, as if use were made of correspondingly wider detector elements. Consequently, the rays from the radiation source to the detector element are wider so that the resolution is degraded (in comparison with the detector unit of FIG. 2a)), because averaging is performed across the surface of the detector elements. An improvement can now be achieved by additional backfolding techniques, for example as used for the correction of detector crosstalk.

The output signals of N (N>2) neighboring detector elements can also be combined. In that case optimum sampling is obtained when use is made of N different combinations with a shift of the group consisting of N detector elements over ¼N, ¾N ... (2N−1)/4N of the width of a detector element. The FIGS. 5a) ... 5d) show the resultant sampling of the Radon space for N=3. In this respect it is assumed that the combination of the output signals of each time three neighboring detector elements per radiation source position produces ten measured values and that 36 measurements from regularly shifted (each time through 10°) radiation source positions are performed for each diagram, the 36 radiation source positions of one diagram being shifted each time 3.33° relative to those of the other diagram.

Figure 5B:
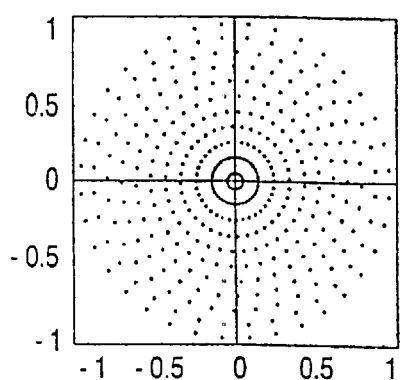
Figure 5C:
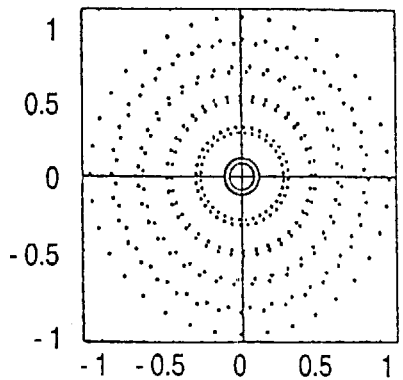
Figure 5D:
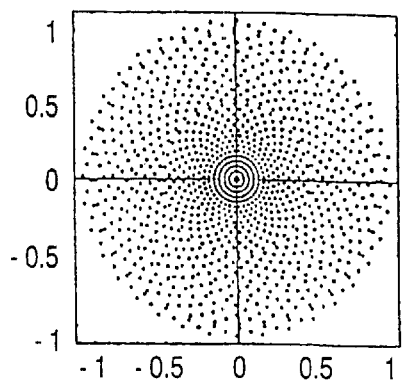

FIG. 5a) shows the diagram for a detector shift amounting to 1/12 detector width; FIG. 5b) shows that for 3/12 and FIG. 5c) that for 5/12 detector width. FIG. 5d) shows the sampling of the Radon space in the case of cyclically changing over between these three combination possibilities upon switching over from one radiation source position to the other. Even though the combination results in the transfer of only ⅓ of the measured values, the sampling of the Radon space in the radial direction is as good as when the output signals of the detector elements are not combined with one another.

According to the described embodiments the output signals of detector elements of each time the same row and two or more neighboring columns were combined. The number of signals to be transferred can also be reduced with significantly less degradation of the spatial resolution when the output signals of detector elements of the same column but neighboring rows are combined. However, the output signals of neighboring rows and neighboring columns can also be combined. This will be described in detail hereinafter with reference to the FIGS. 6a), 6b) and 6c).

Figure 6B:
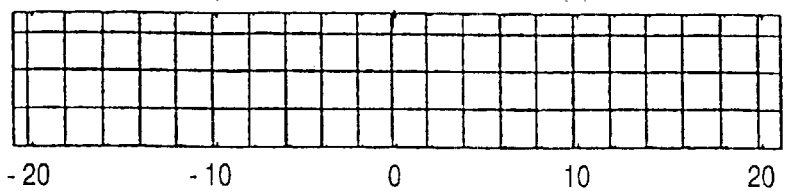
Figure 6C:
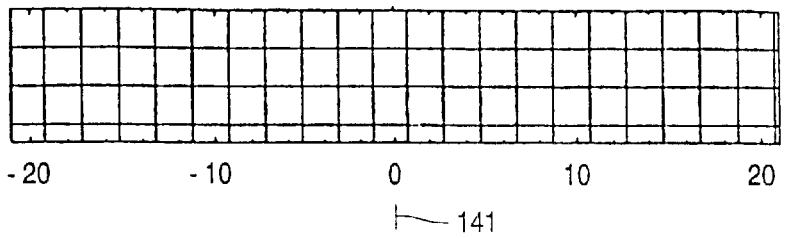

FIG. 6a) again shows the detector unit 16, each square representing a respective detector element. When the output signals of each time two neighboring rows and columns are combined and the surface area of the detector elements thus combined is represented by a square, the arrangement shown in FIG. 6a) becomes that shown in FIG. 6b) or that shown in FIG. 6c). FIGS. 6b) and 6c) deviate from one another in that the rows as well as the columns whose detector elements are combined are interchanged. The resultant squares are shifted relative to one another in the row direction and in the column direction over each time the dimensions of one detector element as shown in FIG. 6a). The number of measured values to be transferred is then reduced to ¼, without the spatial resolution being reduced to the same extent.

FIG. 7 shows diagrammatically a part 160 of a detector unit which includes a number of detector elements in a matrix arrangement. The measured value of a detector element can be read out when the horizontal switching line associated with the relevant detector element is activated and when the signal on the read-out line connected to this detector element is processed. In order to enable combination of the output signals of each time two detector elements which neighbor one another in the horizontal direction and each time two detector elements which neighbor one another in the vertical direction, each time two switching lines can be connected, via an electronic pair of switches $S_V$, in a first switch position to a switching line $L_V$. Similarly, each time two read-out lines can be connected to a common read-out line $L_H$, via a pair of switches, in a first mode of operation, the read-out lines being connected to electronic processing means (for example, read-out amplifiers, multiplexers etc.) which are not shown. In a second mode of operation the switches are switched in the direction of the arrow, so that each time two other neighboring switching lines of the detector unit 160 are connected to the common switching line $L_V$ and each time two other read-out lines are connected to the common read-out line $L_H$.

What is claimed is:

1. A computed tomography method comprising the steps of:

generating, using a radiation source, a radiation beam which traverses at least one of an examination zone and an object present therein, generating a relative motion, including a rotation about an axis of rotation, between the radiation source on the one side and the examination zone or the object on the other side, acquiring measured values for a plurality of radiation source positions by means of a detector unit which is coupled to the radiation source and which includes at least one row of detector elements, combining the signals of each time at least two neighboring detector elements so as to form one measured value, and cyclically varying the combinations of signals from one radiation source position to another.

2. The computed tomography method according to claim 1, further comprising the step of:

shifting a projection of an axis of rotation on the detector unit one quarter of the width of a detector element relative to the center of the detector unit.

3. The computed tomography method according to claim 1, further comprising the steps of:

combining the signals from detector elements in neighboring columns of the detector unit.

4. A computed tomography apparatus comprising:

a radiation source for generating a radiation beam which traverses an examination zone or an object present therein, a drive unit for realizing a relative motion, including a rotation about an axis of rotation, between the radiation source on the one side and the examination zone or the object on the other side, a detector unit which is coupled to the radiation source and includes at least one row of detector elements for the acquisition of measured values for a plurality of radiation source positions, wherein the apparatus includes a combination device for combining the signals of each time at least two neighboring detector elements so as to form one measured value, and means for cyclically varying the combinations of signals from one radiation source position to another.

5. The computed tomography apparatus as claimed in claim 4, wherein the radiation source includes a diaphragm device for forming a conical radiation beam, and the detector unit includes a plurality of rows of detector elements.

6. The computed tomography apparatus as claimed in claim 4, wherein the combination device is constructed in such a manner that the signals from detector elements in neighboring columns of the detector unit are combined.

7. The computed tomography apparatus as claimed in claim 6, wherein the radiation detector is arranged relative to the radiation source and the axis of rotation in such a manner that the projection of the axis of rotation on the detector unit is shifted one quarter of the width of a detector element relative to the center of the detector unit.

8. The computed tomography apparatus as claimed in claim 4, wherein the combination device is constructed in such a manner that the signals from detector elements in neighboring rows of the detector unit are combined.

9. The computed tomography apparatus as claimed in claim 4, wherein the radiation detector is arranged relative to the radiation source and the axis of rotation in such a manner that the projection of the axis of rotation on the detector unit is shifted one quarter of the width of a detector element relative to the center of the detector unit.

* * * * *